United States Patent [19]

Ho

[11] Patent Number: 5,135,662
[45] Date of Patent: Aug. 4, 1992

[54] TUBE CLARIFIER METHOD FOR MONITORING AND/OR CONTROLLING CLARIFICATION PROCESSES

[76] Inventor: Bosco P. Ho, 2618 Siesta Dr., Pittsburgh, Pa. 15241

[21] Appl. No.: 592,756

[22] Filed: Oct. 4, 1990

[51] Int. Cl.$^5$ .............................................. B01D 21/32
[52] U.S. Cl. .................... 210/709; 73/865.9; 210/745; 210/917
[58] Field of Search .............. 210/85, 94, 96.1, 143, 210/198.1, 521, 522, 709, 738, 745, 917; 73/61.4, 865.5, 865.9

[56] References Cited

U.S. PATENT DOCUMENTS

| | | | |
|---|---|---|---|
| 3,812,966 | 5/1974 | Beach et al. | 210/745 |
| 4,576,723 | 3/1986 | Eisenlauer et al. | 210/745 |
| 4,752,131 | 6/1988 | Eisenlauer et al. | 356/330 |
| 4,818,392 | 4/1989 | Werner et al. | 210/521 |
| 4,851,128 | 7/1989 | Rose | 210/917 |
| 4,976,871 | 12/1990 | Banks et al. | 210/709 |

FOREIGN PATENT DOCUMENTS

| | | | |
|---|---|---|---|
| 651828 | 3/1979 | U.S.S.R. | 210/96.1 |
| 2129549 | 5/1984 | United Kingdom | 210/709 |

OTHER PUBLICATIONS

Rank Brothers Ltd. bulletin "Photometric Dispersion Analyzer PDA 2000", 4-89.

Primary Examiner—Robert A. Dawson
Assistant Examiner—Joseph Drodge

[57] ABSTRACT

An on-line monitoring/control method for a separation process used to remove solids from a carrier liquid, wherein a portion of an influent stream containing both the carrier liquid and solids is diverted through a tube after addition of a separation agent, causing slugs of solids to form in the tube which are carried through the tube by clarified carrier liquid in plug flow, and wherein the clarity of the clarified carrier liquid is used to monitor or control the separation process.

7 Claims, 1 Drawing Sheet

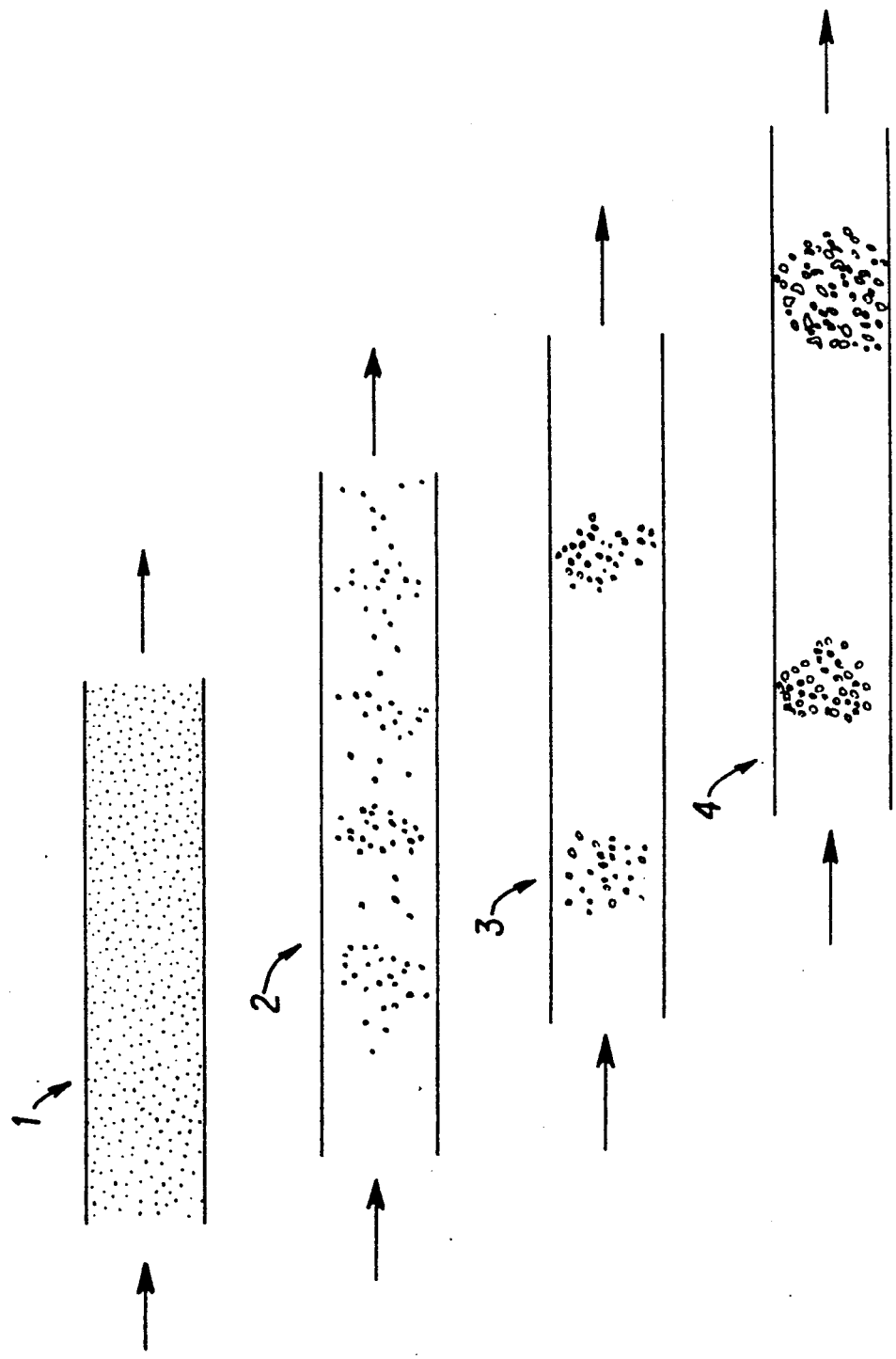

TUBE CLARIFIER METHOD FOR MONITORING AND/OR CONTROLLING CLARIFICATION PROCESSES

BACKGROUND OF THE INVENTION

The use of coagulants or flocculants to clarify aqueous systems is well known in the art. For example, these agents can be used to remove solids such as color bodies from pulp/papermill and municipal wastewater systems. However, the ability to simply, inexpensively and automatically control the feed of coagulants or flocculants to such systems based on an on-line indication of the effluent quality of the system being treated is not believed to be presently available. Such a capability would constitute a notable advance of the art. For example, it would be desirable to regulate the dosage of a coagulant or flocculant so as to achieve an effluent color or turbidity specification, while minimizing the costs associated with coagulant/flocculant application. The instant invention, which relies upon a tube clarifier to monitor and/or control clarification efficacy, accomplishes this objective.

Generally speaking, the instant invention relates to the separation or removal of solids such as suspended matter and/or color bodies from aqueous systems. As used herein, the term "separation process" is used to describe such processes. A preferred separation process, relative to use of the instant method, is a clarification process.

The prior art relies on the following methods to monitor clarification processes:

(a) Laboratory evaluation, which requires the taking of a sample, followed by measurement of effluent quality.

(b) Small scale simulation of the process, wherein a coagulant-treated stream is split and the side stream is passed through a small scale liquid-solid separation process, such as a small solids contact clarifier, filter, or settling chamber. The quality of the separated effluent is then measured. An example of such a device, where a small filter is used prior to turbidity measurement, is disclosed in "Water Treatment and Plant Design for the Practicing Engineer," Ann Arbor Science publishers, Inc. (1978) pp.300-302.

(c) Charge measurement by streaming current, wherein a side stream of a treated stream is passed through a streaming current measurement device. Charge neutralization is an indication of the expected effluent quality.

The streaming current principle is oftentimes used in applications where the suspended solids are low, where the water is clean (i.e., does not contain substantial amounts of oil or other municipal or industrial waste), and where the coagulant and flocculant dosages are low. However, the inventor is not aware of applications or publications which describe a successful use of stream current measurement in more severe applications.

(d) Flocculation analyzers which quantify the extent of flocculation by measuring changes in the number of solids particles present (e.g., particle counts) during a separation process.

These monitoring methods have several disadvantages. For example, the manual methods conducted in a laboratory cannot be run on a continuous basis. Small scale simulation techniques are expensive, and the complexity and reliability of related equipment generally precludes unattended operation.

While streaming current measurement has been found to be applicable in certain feed water clarification applications, such as in the clarification of drinking water and utility water for industrial plants, it has not been found to be applicable in the treatment of streams that contain high amounts of solids, waste treatment, or treatments requiring a high dosage of coagulant or flocculant. Finally, flocculation analyzers require sophisticated instrumentation. They function by incrementally increasing coagulant dosages in the sampled stream with concurrent observation of the resulting changes in effluent quality. The proper dosage is then inferred from the response, which is time-consuming and costly. These disadvantages are overcome by the instant invention.

Known references relating to the flocculation analyzers include:

UK 2,129,549 (May 1984) John Gregory & David William Nelson of University College London, "Detecting Particles And Changes In Particle Size In A Suspension"; and U.S. Pat No. 4,752,131 (June 1988) J. Eisenlauer, D. Horn, W. Ditter & H. Eipel, "Laser System For Particle Dispersion Measurement Has Optical Fibres For Transmission From Laser And To Detector With Sample Flow Surrounded By Envelope Flow".

Also, commercially available flocculation analyzers include the Photometric Dispersion Analyzer PDA 2000, Rank Brothers Ltd., Cambridge, England, and the Flocculation Analyzer System 6000 from Pen Kem, Inc. Bedford Hills, N.Y. Settling devices known in the art include settling tubes, Lamellae sedimentation devices, and inclined plate clarifiers. However, the instant use of tube clarifiers is completely novel.

For a discussion of settling tubes, see "Water Treatment and Plant Design for the Practicing Engineer," Ann Arbor Science Publishers, Inc. (1978) pp. 178-179, 302-307. These devices enhance the separation of clarified effluent from sedimenting solids. However, a key distinction between these devices and the instant tube clarifier is that the instant tube clarifier allows coagulation and/or flocculation to go to completion without physical separation of the effluent from the solids. Also, in the instant method, slugs of solids are carried by the carrier liquid.

DESCRIPTION OF THE FIGURE

FIG. 1 illustrates the formation of solid slugs in the instant tube clarifier.

SUMMARY OF THE INVENTION

A method and system for monitoring and/or controlling a separation process is disclosed. In such a process, for example a clarification process, an influent stream comprising a carrier liquid and solids is treated with an agent to effectuate separation of the solids from the liquid carrier. In the instant method, the influent stream of a separation process is split, after treatment with the separation enhancing agent (e.g., a coagulant and/or flocculant) into a main stream, which is treated by the separation process, and a side stream. The side stream is passed through a tube (hereinafter also referred to as a tube clarifier), wherein separation or segregation of the solids into slugs of solids occurs. The slugs of solids are then carried by the clarified carrier liquid by or through a means for determining the degree of separation or segregation which occurs in the tube. This means, which is preferably a turbidimeter, is preferably located near the end or at the exit of the tube. Also, the cell of such a means may be an integral part of the tube. Aside from the discovery that slugs of solids form in the tubes of this invention and that the slugs travel in plug flow through such tubes, the inventor has discovered that the clarified carrier liquid carrying the slugs is generally representative of the effluent from the overall separation process. Thus, by monitoring the clarified carrier liquid, the slugs of solids, or both (i.e., the complete side stream), one can monitor and/or control the efficacy of the overall separation process.

DETAILED DESCRIPTION OF THE INVENTION

The instant invention relates to a method for on-line monitoring and/or control of a separation process, preferably a clarification process, wherein an influent stream comprising a carrier liquid and solids (suspended, dissolved and/or colloidal) is treated with at least one separation agent such as a coagulant and/or a flocculant to effectuate removal of said solids from said carrier liquid, which method comprises:

(a) diverting a portion of said influent stream, after treatment with said separation agent, through a tube having an effective diameter and length for the purpose of forming substantially discrete slugs of solids in said tube, thereby causing the formation of substantially discrete slugs of solids in said tube as the diverted portion of said influent stream passes through said tube and wherein said slugs of solids are carried by clarified carrier liquid in said tube;

(b) determining the degree of solids separation of the diverted portion of said influent stream, either while said portion is in or after it exits said tube, preferably by determining, visually or otherwise, its clarity though a measurement of the color, reflectance, absorbance, transmittance, turbidity etc., of one or more components of said portion, or, alternatively and preferably, by determining the clarity of the clarified carrier liquid component of said portion;

(c) relating the degree of separation, or preferably the clarity, of said portion, or component thereof, preferably the clarity of said clarified carrier liquid, to the separation efficacy or performance of said separation process and using said clarity to monitor the efficacy of said separation process; and (d) optionally, controlling the addition of said separation agent based on the clarity of said portion or component thereof or, preferably, said clarified carrier liquid.

The instant invention also relates to a system comprising: a) a separation process having an influent stream comprising a carrier liquid, a separation agent and solids; b) a tube, through which a portion of said influent stream is passed, wherein solids in said portion form substantially discrete solids slugs; c) a means for determining the degree of solids separation in said portion or one or more components of said portion; and d) optionally, an output device which monitors and or controls said separation process. Such a system enables one to practice the instant method.

In its broadest sense, the present invention may be utilized to monitor and/or control any separation process, but is preferably used to monitor and/or control a clarification process. In a typical clarification process, a separation agent, such as a flocculant or coagulant, is fed at an effective dosage to a carrier liquid containing solids to effectuate the desired separation of the solids from the carrier liquid. The carrier liquid is generally water, though the instant invention is not so limited. As used herein, the term "solids" refers to any solid material present in a carrier liquid which imparts color or turbidity to that carrier liquid. Examples of solids include, but are not limited to, color bodies, suspended solids and/or colloidal solids. Typical separation agents include, but are not limited to, polymeric agents and alum.

Clarification applications include, but are not limited to, municipal sewage treatment, treatments in the ore and oil industries, treatments of latex emulsions and industrial waste treatments such as those which occur in petrochemical plants, textile mills, pulp and paper mills and sugar refining applications. The clarification process equipment that can be used includes but is not limited to clarifiers, upflow clarifiers, solids-contact clarifiers, settling basins, air flotation systems, dissolved air flotation systems, dewatering equipment and other liquid/solid separation equipment.

The instant inventor has discovered that, by diverting a portion of the carrier liquid to be separated or clarified through a tube having an effective diameter and length, the separation efficiency of the clarification process can be monitored and/or controlled. Thus, when a carrier liquid containing solids and a separation agent such as a coagulant or flocculant is caused to flow through a tube of effective diameter and length, the solids tend to form or to separate into slugs of solids which are carried through the tube by clarified carrier liquid. Ideally, these slugs move in plug flow, as shown in FIG. 1. Initially, the solids are dispersed throughout the carrier liquid in the tube clarifier. This is shown by 1 in FIG. 1. Discrete flocs then begin to form, as shown by 2, followed by formation of solids slugs (3) as flocculation continues. Finally, substantially discrete slugs of solids form and are transported through the tube by clarified carrier liquid (4 in FIG. 1).

The inventor has also discovered that the quality of the clarified carrier liquid carrying the slugs of solids through the tube is generally representative of the effluent from the overall separation process. Thus, by preferably determining the clarity of the clarified carrier liquid, either inside the tube or after it exits the tube, preferably near the exit of the tube, by measuring its color, turbidity, reflectance transmittance, absorbance, etc., one skilled in the art can utilize the tube clarifier as an on-line device for monitoring overall separation performance. Alternatively, the characteristics of the solids slugs or the overall stream can be related to separation process efficacy. Further, the overall process can be controlled based on the tube clarifier readings. For example, the clarity of the clarified carrier liquid can be used to control the dosage of the coagulant or flocculant being fed so as to bring overall clarification performance into specification and to maintain it within designated limits.

The instant invention represents a simple, accurate and novel method and system for on-line monitoring and/or control of a separation process without the need for a mini-clarifier. The essence of this invention is that solids separation or segregation occurs when a split stream of a flocculant or coagulant-treated carrier liquid is caused to flow through a tube. Resulting from this solids separation or segregation, slugs of solids are formed which are carried in substantially plug flow by clarified carrier liquid. Color, reflectance, turbidity, transmittance, absorbance or some other measure of the degree of separation in the tube, for example the clarity of the clarified carrier liquid, can be related to overall separation efficacy and used to monitor and/or control the separation process. Preferably, a means for determining the clarity of the clarified carrier liquid, such as a turbidimeter, is located at or near the exit of the tube and used to measure the clarity of the clarified carrier liquid. In its simplest sense, visual observations can be made to monitor efficacy of the separation process. Preferably, the turbidimeter generates a signal to an output device such as a monitor or process controller.

Since the clarity readings of the clarified carrier liquid are interrupted periodically by slugs of solids, a means for discounting the readings obtained as the slugs of solids pass through or by the clarity determining means is necessary to accurately depict separation efficacy if the stream flowing in the tube is continuously analyzed. For example, a data reduction computer software program may be utilized to eliminate the interruptions caused by the solids slugs. Such techniques are well within the abilities of those skilled in the art. The inventor has discovered that the characteristics of the clarified carrier liquid flowing in the tube clarifier generally correspond closely to those of the effluent from the clarification process. Thus the tube-clarifier can be readily used used for on-line monitoring and/or control of the overall process.

Since turbidimeter devices, and other devices used to monitor clarity, are likely to become fouled, especially on the glass cell where the stream passes through or contacts the light path, an automatic cleaning device can be used if such fouling occurs frequently enough that periodic manual cleaning is not practical.

A tube of effective length and diameter should be used. Relative to the tube length and diameter, the term "effective" refers to the length and diameter of the tube which allows for the formation of substantially discrete slugs of solids which move through the tube substantially in plug flow. Numerous experiments were conducted by the inventor to observe the effect of several parameters, including volumetric flow rate, linear velocity tube diameter and tube length, on performance. Based on these experiments, the inventor has discovered that tube-clarifier design should ideally balance the need for low tubular volume (i.e., low residence time) with the need for longer separation between the slugs (i.e., increase the time to obtain a correct clarity reading between the interruptions caused by the slugs). In summary, it has been found that reducing the flow through the tube enhances flocculation since shear is reduced, but that, when the flow is too low, the residence time is too high. Increasing tube diameter reduces the shear. However, if the diameter becomes too large, the solids slugs formed may not be large enough to be carried in a plug-flow manner, which causes the slugs to break up periodically. This can be easily eliminated by proper choice of tube diameter in light of the amount of sludge solids generated. An effective tube diameter (ID) and length should be used, based upon the volumetric flow rate of the side stream, the solids loading, the carrier liquid and the coagulant or flocculant dosage. Tube length should yield a residence time of between about 1 and 20 minutes, preferably about 2 to 8 minutes. Preferably, the tube diameter should range between about 1/16" and about ⅜" ID, more preferably between about 5/32" and about ¼". Also, by stepping down the tube diameter (e.g., from 5/16 inch ID to 3/16 inch ID) in the middle of the tube, slugs are generally further combined yielding larger separation between slugs. By running the tube vertically, the gravity effect generally helps to separate slugs of solids into discrete plugs. The preferred orientation of the tube causes the diverted portion of the influent stream to spiral upward toward the means for determining clarity.

The tube may be constructed of any material compatible with the carrier liquid, solids and the separation agent. Clear, plastic tubing or glass tubing is preferred. A tube-clarifier configuration which is exemplary of the best mode meets the following specifications:

| | |
|---|---|
| Carrier liquid + solids + coagulant flow rate: | 80 ± 20 ml/minute |
| Tube dimensions: | 10 ft. long of 5/16 inch ID |
| (from inlet) | 10 ft. long of 3/16 inch ID |
| | 10 ft. long of 5/16 inch ID |
| | 14 ft. long of 3/16 inch ID |
| Residence time: | About 4 minutes |
| Orientation: | Tube spiraling upward with flow from bottom to top, turbidity readings at the end of the tube. |

Typical results obtained from such an arrangement include the formation of discrete slugs of solids, wherein slug separations are about 1 ft. to about 5 ft. The time between turbidity reading interruptions thus ranges from about 5 seconds to about 25 seconds.

Clarity measurements of the clarified carrier liquid are not restricted to turbidity. For example, transmittance, color, reflectance or absorbance can be used, but the invention is not so limited. Generally speaking, any measurement of the degree of separation or clarity can be used. Also, visual observation and measurement may be acceptable in some applications. Further, the measurement is not restricted to the clarified carrier liquid; the degree of separation or segregation (clarity) measurement can be made on the slugs of solids alone or on the overall stream in the tube. Preferably, the means for determining the degree of separation or clarity generates a signal which is then fed to a monitoring and/or control device.

A restriction at the exit of the tube, but before the sensing device, can be used to cause the breakup of the solids. The breakup of the solids in turn affects the ability of the solids to resist shear degradation known as "floc strength". Thus the invention can also be used to monitor floc strength.

EXAMPLES

The following example further illustrates the instant invention, but should not be construed as limiting the instant invention in any way. The instant tube clarifier was used to monitor a separation process used to remove color bodies from pulp and paper mill wastewater. In this process, a coagulant was added to the wastewater via a rapid mix tank, which was followed by a conditioning tank. Then a flocculant was added, which was followed by another conditioning tank. The liquid/solid separation was then carried out in a dissolved flotation system which has a residence time of about 90 minutes.

The apparatus of the instant invention was fed by a sample stream drawn immediately after flocculant addition. The apparatus comprised three lengths of tubing in this order: 10 ft of 5/16 inch internal diameter, 10 ft of ¼ inch internal diameter, and 10 ft of 5/16 inch internal diameter. The tube effluent was then passed through a turbidity sensor with a straight-through flow cell of 9 mm internal diameter. An automated cleaning brush was used to clean the internal diameter of the flow cell. The turbidity sensor read the clarified effluent turbidity with intermittent disturbances from the slugs of solids. A signal conditioning software program was used to effectively eliminate the effect of the slugs of solids thus providing turbidity values for the clarified carrier liquid. These turbidity values were then related to the turbidity of the effluent from the overall process by direct comparison of the tube readings with the overall process readings at any given time. This enabled the turbidity values to be used to monitor the separation process.

What is claimed is:

1. A method for on-line monitoring or control of a separation process wherein an influent stream comprising a carrier liquid and solids is treated with a separation agent to effectuate removal of some amount of said solids from said carrier liquid, which method comprises:
   (a) diverting a portion of said influent stream, after treatment with said separation agent, through a tube having an effective diameter and length for forming substantially discrete slugs of solids in said tube, thereby causing formation of slugs of solids in said tube as the diverted portion of said influent stream passes through said tube and wherein said slugs of solids are carried by clarified carrier liquid in said tube in substantially plug flow,
   (b) determining the degree of solids segregation in said portion either while said portion is in or after it exits said tube;
   (c) relating said degree of solids segregation performance of said separation process; and
   (d) monitoring or controlling said separation process based on said degree of segregation.

2. The method of claim 1, wherein said separation process is a clarification process.

3. The method of claim 2, wherein said separation agent is a flocculant and/or a coagulant.

4. The method of claim 2, wherein the degree of solids segregation is determined by measuring the clarity of said clarified carrier liquid.

5. The method of claim 4, wherein the clarity of said clarified carrier liquid is determined by measuring its turbidity.

6. The method of claim 5, wherein said clarification process separates color bodies from papermill wastewater or municipal wastewater.

7. The method of claim 2, wherein said clarification process separates color bodies from papermill wastewater or municipal wastewater.

* * * * *